United States Patent
Nagano et al.

(10) Patent No.: US 8,725,233 B2
(45) Date of Patent: May 13, 2014

(54) LOAD DETECTION DEVICE AND LOAD DETECTION METHOD

(75) Inventors: Yoshitaka Nagano, Iwata (JP); Yukihiro Nishio, Iwata (JP); Takayoshi Ozaki, Iwata (JP)

(73) Assignee: NTN Corporation, Osaka (JP)

(*) Notice: Subject to any disclaimer, the term of this patent is extended or adjusted under 35 U.S.C. 154(b) by 749 days.

(21) Appl. No.: 12/808,125

(22) PCT Filed: Dec. 4, 2008

(86) PCT No.: PCT/JP2008/072030
§ 371 (c)(1),
(2), (4) Date: Jun. 14, 2010

(87) PCT Pub. No.: WO2009/078280
PCT Pub. Date: Jun. 25, 2009

(65) Prior Publication Data
US 2010/0292566 A1    Nov. 18, 2010

(30) Foreign Application Priority Data

Dec. 14, 2007 (JP) ................. 2007-323670
Oct. 15, 2008 (JP) ................. 2008-266365

(51) Int. Cl.
- *A61B 5/05* (2006.01)
- *A61B 5/103* (2006.01)
- *A61M 29/00* (2006.01)

(52) U.S. Cl.
USPC .......................... 600/424; 600/587; 606/191

(58) Field of Classification Search
USPC .................. 600/424, 587; 606/191
See application file for complete search history.

(56) References Cited

U.S. PATENT DOCUMENTS

| | | | |
|---|---|---|---|
| 6,117,157 A * | 9/2000 | Tekulve | 606/200 |
| 2001/0029334 A1* | 10/2001 | Graumann et al. | 600/437 |
| 2002/0114920 A1* | 8/2002 | Scholz et al. | 428/119 |
| 2003/0040737 A1 | 2/2003 | Merril et al. | |
| 2006/0200049 A1 | 9/2006 | Leo et al. | |
| 2007/0021742 A1 | 1/2007 | Viswanathan | |
| 2008/0043902 A1* | 2/2008 | Viswanathan | 378/20 |

FOREIGN PATENT DOCUMENTS

| | | | |
|---|---|---|---|
| JP | 10-263089 | 10/1998 | |
| JP | 2007292711 A * | 11/2007 | G01L 5/04 |
| JP | 2008-185360 | 8/2008 | |
| WO | WO 2006/020792 A2 | 2/2006 | |
| WO | WO 2007/111182 A1 | 10/2007 | |

OTHER PUBLICATIONS

European Search Report issued in European Patent Application No. 08861483.9 dated Nov. 14, 2011.

* cited by examiner

*Primary Examiner* — Long V. Le
*Assistant Examiner* — Bo J Peng
(74) *Attorney, Agent, or Firm* — McDermott Will & Emery LLP (57) ABSTRACT

According to this load detection method, load (Fi) in insertion of a linear body having flexibility in an inlet of a hollow tube inserted in a bending vessel in a body is detected, an image of the hollow tube or the linear body is taken, a degree of bending of the hollow tube or the linear body is detected based on the image, and load (Fo) at a tip end of the linear body is calculated based on the detected insertion load (Fi) and the degree of bending. Therefore, the load (Fo) at the tip end of the thin linear body can readily be detected.

17 Claims, 12 Drawing Sheets

LOAD DETECTION DEVICE AND LOAD DETECTION METHOD

RELATED APPLICATIONS

This application is the U.S. National Phase under 35 U.S.C. §371 of International Application No. PCT/JP2008/072030, filed on Dec. 4, 2008, which in turn claims the benefit of Japanese Application Nos. 2007-323670, filed on Dec. 14, 2007 and 2008-266365, filed on Oct. 15, 2008, the disclosures of which Applications are incorporated by reference herein.

TECHNICAL FIELD

The present invention relates to a load detection device and a load detection method, and particularly to a load detection device and a load detection method for detecting load applied to a tip end of a linear body having flexibility in inserting the linear body in a hollow tube inserted in a bending vessel.

BACKGROUND ART

A catheter has conventionally been put into practical use as a linear medical appliance to be inserted in a vessel in a body such as a blood vessel, a ureter, a bronchus, an alimentary canal, or a lymph vessel. Among treatment methods using a catheter, for example, a method of preventing rupture of a cerebral aneurysm by guiding a tip end of a catheter representing a hollow tube to a mouth of the cerebral aneurysm through a blood vessel from outside a body, thereafter inserting an embolization coil and a delivery wire representing linear bodies having flexibility in the catheter, and filling the cerebral aneurysm with the embolization coil is available. If excessive load is applied to the cerebral aneurysm by the embolization coil and the delivery wire, however, the cerebral aneurysm may be damaged.

In addition, a method of providing a pressure sensor at a tip end of a catheter is available as a method of detecting load at the tip end of the catheter (see, for example, Japanese Patent Laying-Open No. 10-263089 (Patent Document 1)).

Patent Document 1: Japanese Patent Laying-Open No. 10-263089

DISCLOSURE OF THE INVENTION

Problems to be Solved by the Invention

It is extremely difficult, however, to provide a pressure sensor at the tip end of a thin embolization coil and to insert in the embolization coil a signal line for extracting a signal from the pressure sensor to the outside.

Therefore, a primary object of the present invention is to provide a load detection device and a load detection method capable of readily detecting load applied to a tip end of a thin linear body.

Unit for Solving the Problems

A load detection device according to the present invention is a load detection device for detecting load applied to a tip end of a linear body having flexibility when the linear body is inserted in a hollow tube inserted in a bending vessel, and the load detection device includes first detection unit for detecting a degree of bending of the vessel, the hollow tube or the linear body, second detection unit for detecting load in insertion of the linear body in an inlet of the hollow tube, and calculation unit for finding load applied to the tip end of the linear body based on a result of detection by the first and second detection unit.

Preferably, the first detection unit detects the degree of bending of the vessel, the hollow tube or the linear body based on an image of the vessel, the hollow tube or the linear body.

In addition, preferably, the calculation unit finds the load applied to the tip end of the linear body further based on a coefficient of friction between the linear body and the hollow tube.

In addition, preferably, the calculation unit corrects the coefficient of friction based on variation in flexural rigidity depending on a position in the linear body when the flexural rigidity of the linear body varies depending on the position in the linear body.

In addition, preferably, the coefficient of friction is measured in advance.

In addition, preferably, the vessel is a blood vessel, the hollow tube is a catheter, and the linear body is a treatment wire to be inserted in the catheter.

In addition, preferably, the treatment wire includes a delivery wire and an embolization coil provided at a tip end portion of the delivery wire, for filling a cerebral aneurysm.

In addition, preferably, the first detection unit detects a degree of bending of the treatment wire when a tip end of the embolization coil enters the cerebral aneurysm, and the calculation unit finds load applied to the cerebral aneurysm by the embolization coil.

In addition, preferably, the first detection unit detects a degree of bending of the blood vessel based on a three-dimensional image of the blood vessel.

In addition, preferably, the first detection unit detects a degree of bending of the treatment wire based on a two-dimensional image of the treatment wire taken by using X-rays during a surgical operation and a three-dimensional image of the blood vessel taken in advance, as superimposed on each other.

In addition, preferably, the load detection device includes drive unit for inserting the linear body in the inlet of the hollow tube, and the second detection unit detects the load in insertion of the linear body based on drive force of the drive unit.

In addition, preferably, the load detection device includes a drive roller for inserting the linear body in the inlet of the hollow tube, a pressing roller rotatably supported and pressed by the drive roller with the linear body being interposed, and a motor for rotatably driving the drive roller, and the second detection unit detects strain of a rotation shaft of the motor and detects the load in insertion of the linear body based on a result of that detection.

In addition, preferably, the second detection unit includes a main body portion having a through hole through which the linear body passes and an internal space provided at an intermediate point of the through hole and formed such that the linear body can curve in a prescribed direction when compressive force is applied to the linear body, and a curve sensor for detecting a degree of curve of the linear body in the internal space, and detects the load in insertion of the linear body based on the degree of curve detected by the curve sensor.

In addition, preferably, the second detection unit includes a main body portion having a through hole through which the linear body passes and formed in a bent manner such that the linear body applies a pressure in a prescribed direction when compressive force is applied to the linear body, and a pressure sensor provided at an intermediate point of the through hole, for detecting a pressure applied by the linear body in the prescribed direction, and detects the load in insertion of the linear body based on a result of detection by the pressure sensor.

In addition, preferably, the load detection device further includes display unit for visually displaying at least one load of the load in insertion of the linear body detected by the second detection unit and the load applied to the tip end of the linear body found by the calculation unit.

In addition, preferably, the load detection device further includes sound generation unit for generating sound indicating at least one load of the load in insertion of the linear body detected by the second detection unit and the load applied to the tip end of the linear body found by the calculation unit.

In addition, preferably, the load detection device further includes recording unit for recording in a video image recording medium together with an fluoroscopic image of a tip end portion of the linear body, at least one load of the load in insertion of the linear body detected by the second detection unit and the load applied to the tip end of the linear body found by the calculation unit.

In addition, preferably, the load detection device is incorporated in a medical training apparatus.

In addition, a load detection method according to the present invention is a load detection device for detecting load applied to a tip end of a linear body having flexibility when the linear body is inserted in a hollow tube inserted in a bending vessel, and a degree of bending of the vessel, the hollow tube or the linear body and load in insertion of the linear body in an inlet of the hollow tube are detected, and load applied to the tip end of the linear body is found based on a result of that detection.

Effects of the Invention

According to the load detection device and the load detection method of the present invention, a degree of bending of a vessel, a hollow tube or a linear body and load in insertion of the linear body in an inlet of the hollow tube are detected, and load applied to the tip end of the linear body is found based on a result of that detection. Therefore, even when the linear body is thin, load applied to the tip end of the linear body can readily be detected.

DESCRIPTION OF THE REFERENCE SIGNS 1 hollow tube; 2 linear body; 3 catheter; 4 embolization coil; 5 delivery wire; 6 cerebral artery; 7 cerebral aneurysm; 8 Y-connector; 10 X-ray equipment; 1 image synthesis device; 12 degree-of-bending detection device; 13, 56 insertion load detection device; 14 storage device; 15 arithmetic processing unit; 16 display device; 20 aorta; 21 carotid artery; 22 vertebral artery; 23 blood vessel; 24 fluoroscopic two-dimensional image; 25 three-dimensional blood vessel image; 26 path; 27 three-dimensional image; 30 pressing roller; 31 drive roller; 32 motor; 33 torque control circuit; 34 torque sensor; 40, 50 main body portion; 41, 51 through hole; 42, 52 input and output port; 43 restraint portion; 44 space; 45 line sensor; 46 light source device; 47 storage portion; 48 signal generation portion; 53 elastic member; 54 strain sensor; 55 human body; 57, 64 cable; 58 operation device; 59 display; 60 speaker; 61 switch; 62 simulator; and 63 monitor.

BEST MODES FOR CARRYING OUT THE INVENTION

[Embodiment 1]

Figure 1:
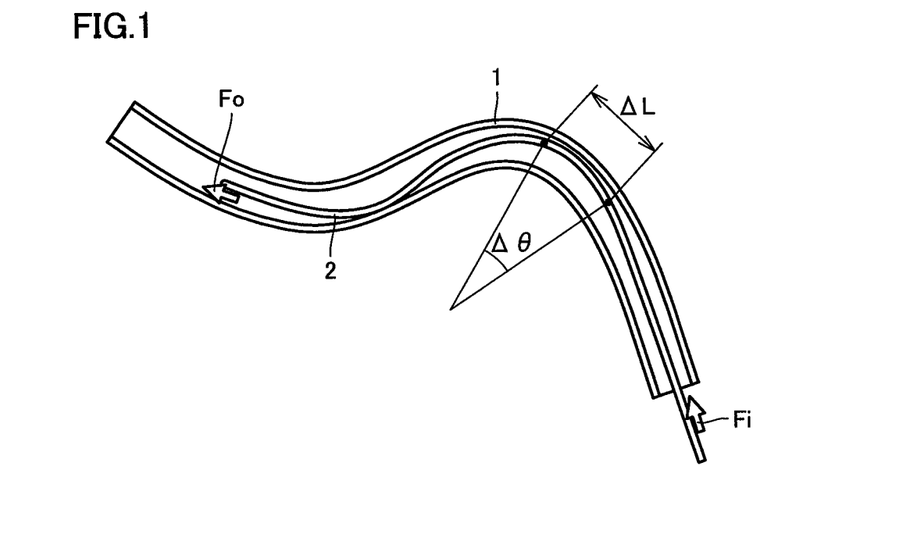
FIG. 1 is a diagram showing a load detection method according to Embodiment 1 of the present invention.

FIG. 1 is a diagram showing a load detection method according to Embodiment 1 of the present invention. In FIG. 1, it is assumed that a hollow tube 1 is inserted in a bending vessel (not shown) in a body and a linear body 2 having flexibility is inserted through an inlet of that hollow tube 1. According to this load detection method, load Fi in insertion of linear body 2 in the inlet of hollow tube 1 is detected, an image of hollow tube 1 or linear body 2 is taken, a degree of bending (for example, $\Delta\theta/\Delta L$) of hollow tube 1 or linear body 2 is detected based on the image, and load Fo at a tip end of linear body 2 is calculated based on detected insertion load Fi and the degree of bending.

Figure 2:
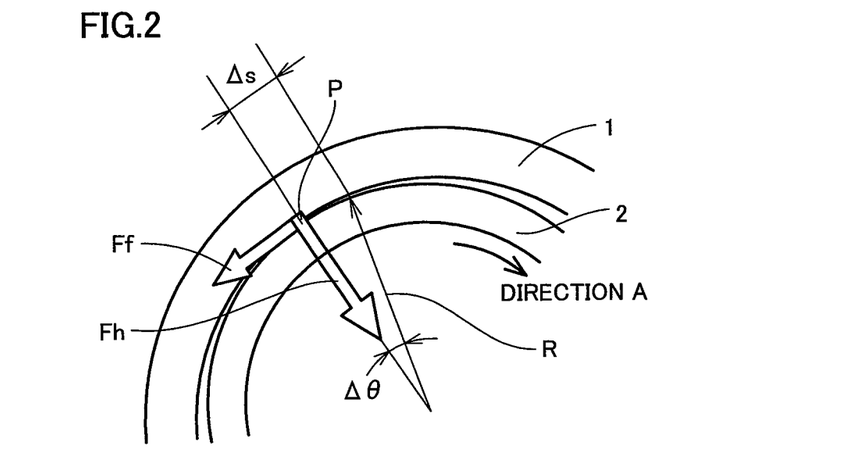
FIG. 2 is a diagram showing a contact point between a hollow tube and a linear body shown in FIG. 1.
Figure 3:
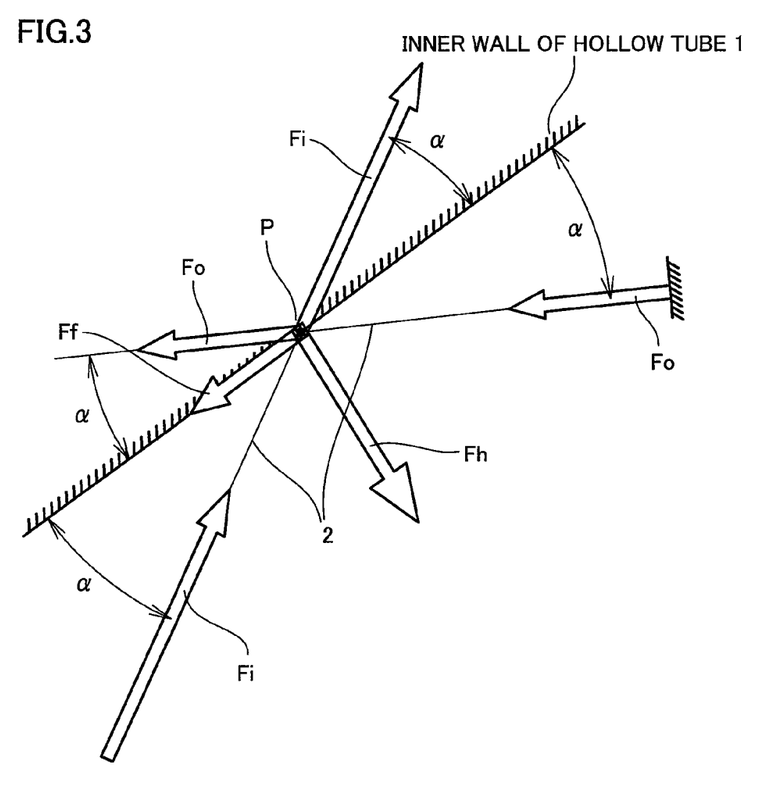
FIG. 3 is a diagram showing balance of forces applied to the contact point shown in FIG. 2.

Specifically, as shown in FIG. 2, in a case where an inner wall of hollow tube 1 comes in contact with linear body 2 at one position of a point P, as linear body 2 is moved in a direction A in FIG. 2, friction force Ff is generated between the inner wall of hollow tube 1 and linear body 2 owing to normal reaction Fh of linear body 2. Relation between normal reaction Fh, friction force Ff and input load Fi, output load Fo of linear body 2 is as shown in FIG. 3. Input load Fi and output load Fo are loads applied to linear body 2 in the front and the rear of point P. Denoting an angle between linear body 2 and hollow tube 1 at point P as α, the following equations (1) and (2) are satisfied based on balance among these forces Fh, Ff, Fi, and Fo.

$$-Ff = Fo \cdot \cos\alpha - Fi \cdot \cos\alpha \quad (1)$$

$$Fh = Fo \cdot \sin\alpha + Fi \cdot \sin\alpha \quad (2)$$

Here, denoting a coefficient of friction as μ, Ff=μ·Fh. In addition, as angle α corresponds to Δθ shown in FIG. 2, the angle can be calculated based on a radius of curvature R and Δs as shown in the following equation (3).

$$|R|/\Delta s = 1/\tan\alpha \quad (3)$$

Summarizing the equations (1) to (3), relation among Fo, Fi, R, Δs, and μ is expressed in the following equation (4).

$$(-\mu/|R|) \cdot \Delta s \cdot (Fo + Fi) = Fo - Fi \quad (4)$$

Here, assuming that a distance from an insertion end of linear body 2 to point P is denoted as s, load applied to linear body 2 at point P is denoted as F(s), and a small distance from point P is denoted as Δs, Fi and Fo are expressed in the following equations (5) and (6), respectively.

$$Fi = F(s) \quad (5)$$

$$Fo = F(s + \Delta s) \quad (6)$$

Here, by substituting the equations (5) and (6) into the equation (4) and assuming that a radius of curvature at position P at distance s is denoted as R(s), the following equation (7) is obtained.

$$(-\mu/|R(s)|) \cdot \Delta s \{F(s+\Delta s) + F(s)\} = F(s+\Delta s) - F(s) \quad (7)$$

Further, by approximating Δs to 0, a differential equation as shown in the following equation (8) is obtained. By solving the differential equation, the following equation (9) showing relation between Fo and Fi at a small distance ds of point P is obtained.

$$dF(s)/ds = -(2\mu/|R(s)|) \cdot F(s) \quad (8)$$

$$Fo = Fi \cdot \exp(-2\mu \int (1/|R(s)|) ds) \quad (9)$$

By using the equation (9), even though portions where friction occurs are continuous, Fo can be found by designating a range of integration. In a case where linear body 2 is inserted in a catheter representing hollow tube 1, since a difference between an inner diameter of hollow tube 1 and an outer diameter of linear body 2 is small, it can conveniently be supposed that linear body 2 is continuously in contact with the inner wall of hollow tube 1.

In addition, when ds is close to 0, tan(dθ) can be approximated to dθ. Therefore, relation between R(s), ds and dθ is as shown in the following equation (10). Here, it is assumed that dθ is described as θ(s, s+ds) and dθ indicates an angle from s to s+ds. By inserting the equation (10) into the equation (9), the following equation (11) is obtained.

$$1/|R(s)| \cdot ds = |\theta(s, s+ds)| \quad (10)$$

$$Fo = Fi \cdot \exp(-2\mu \int (|\theta(s, s+ds)|/ds) ds) \quad (11)$$

In this equation (11), ∫(|θ(s,s+ds)|/ds)ds unit division of small angle θ(s,s+ds) obtained by sectioning linear body 2 or hollow tube 1, from the inlet to the tip end of hollow tube 1, into small lengths ds by that small length ds and integration of that result with small length ds, and hence a result thereof turns out to be a total sum θ of degrees of bending of linear body 2 or hollow tube 1. Based on this equation (11), load Fo at the tip end of linear body 2 can be found based on total sum θ of degrees of bending of linear body 2 or hollow tube 1 from the inlet to the tip end of hollow tube 1 and load Fi in insertion of linear body 2. Since coefficient of friction μ may be different depending on combination of hollow tube 1 and linear body 2, it should only be measured in advance for each combination and selected for use depending on hollow tube 1 and linear body 2 to be used.

Figure 4:
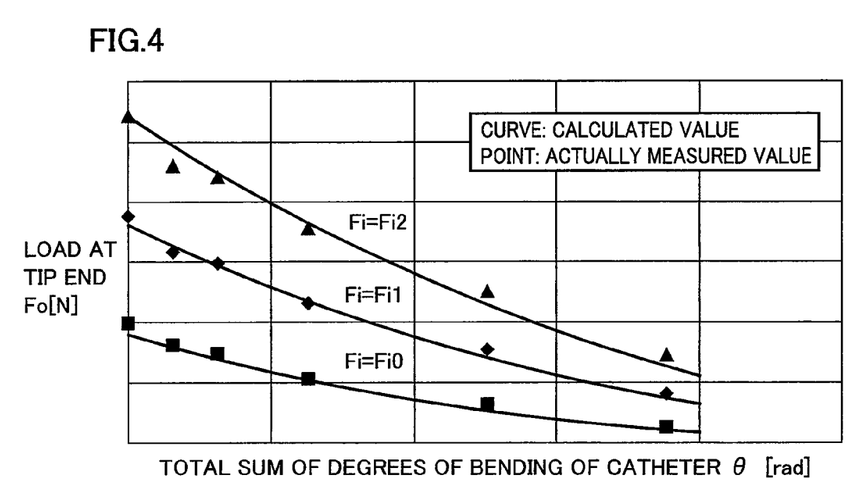
FIG. 4 is a diagram showing a load at a tip end found with the load detection method described in connection with FIGS. 1 to 3 and an actually measured value.

FIG. 4 is a diagram showing relation between total sum θ(rad) of degrees of bending of hollow tube 1 and load Fo(N) at the tip end of linear body 2 in cases where load Fi in insertion of linear body 2 is varied in three steps of Fi0, Fi1 and Fi2 (note the relation of Fi0<Fi1<Fi2). Here, a catheter having an inner diameter Φ0.56 mm is employed as hollow tube 1 and a cerebral aneurysm embolization coil having an outer diameter Φ0.25 mm is employed as linear body 2. Three curves in FIG. 4 represent values calculated by using the following equation (12), and each point represents a measured value.

$$Fo = (Fi - \beta(\theta)) \cdot (\exp(-2\mu\theta) - C) \quad (12)$$

The equation (12) is a corrected version of the equation (11). Here, β(θ) is a function for correcting input load Fi with θ and C is a constant value for correcting influence by friction in an example where linear body 2 is straight (θ=0).

As can be seen in FIG. 4, a calculated value and a measured value are substantially equal to each other. When insertion load Fi is constant, load Fo(N) at the tip end decreases with increase in total sum θ(rad) of degrees of bending of the catheter. Meanwhile, when total sum θ(rad) of degrees of bending of the catheter is constant, load Fo(N) at the tip end also increases with increase in insertion load Fi(N).

Meanwhile, for example, the delivery wire is smaller in diameter at a position close to the tip end of the coil. Namely, flexural rigidity of linear body 2 is not uniform across positions in linear body 2 but is different from position to position. At such a position where flexural rigidity varies, a portion lower in flexural rigidity tends to bend more, which results in greater normal reaction Fh applied to hollow tube 1. In that case, depending on flexural rigidity EI at a position in linear body 2 and variation in flexural rigidity EI, the equation (12) is corrected to the following equation (13). In this case, equivalent μ should only be corrected. Therefore, coefficient of friction μ is expressed as a function of flexural rigidity EI(s), variation in flexural rigidity dEI(s)/ds and R(s), and this function is found in advance in experiments.

$$Fo = Fi \cdot \exp(-2\int \mu(EI(s), dEI(s)/ds, R(s)) \cdot |R(s)| ds) \quad (13)$$

In present Embodiment 1, degree of bending θ of hollow tube 1 or linear body 2 and load Fi in insertion of linear body 2 in the inlet of hollow tube 1 are detected, and load Fo applied to the tip end of linear body 2 is found based on the result of detection. Therefore, load Fo applied to the tip end of thin linear body 2 can readily be detected. Thus, an operator who is a doctor can accurately operate linear body 2 based on a detection value of load Fo at the tip end of linear body 2 and such medical malpractice as damaging a cerebral aneurysm or the like with the tip end of linear body 2 is prevented. In addition, as it is not necessary to attach a pressure sensor at the tip end, conventional linear bodies 2 can be used as they are and detection at low cost can be made.

[Embodiment 2]

Figure 5:
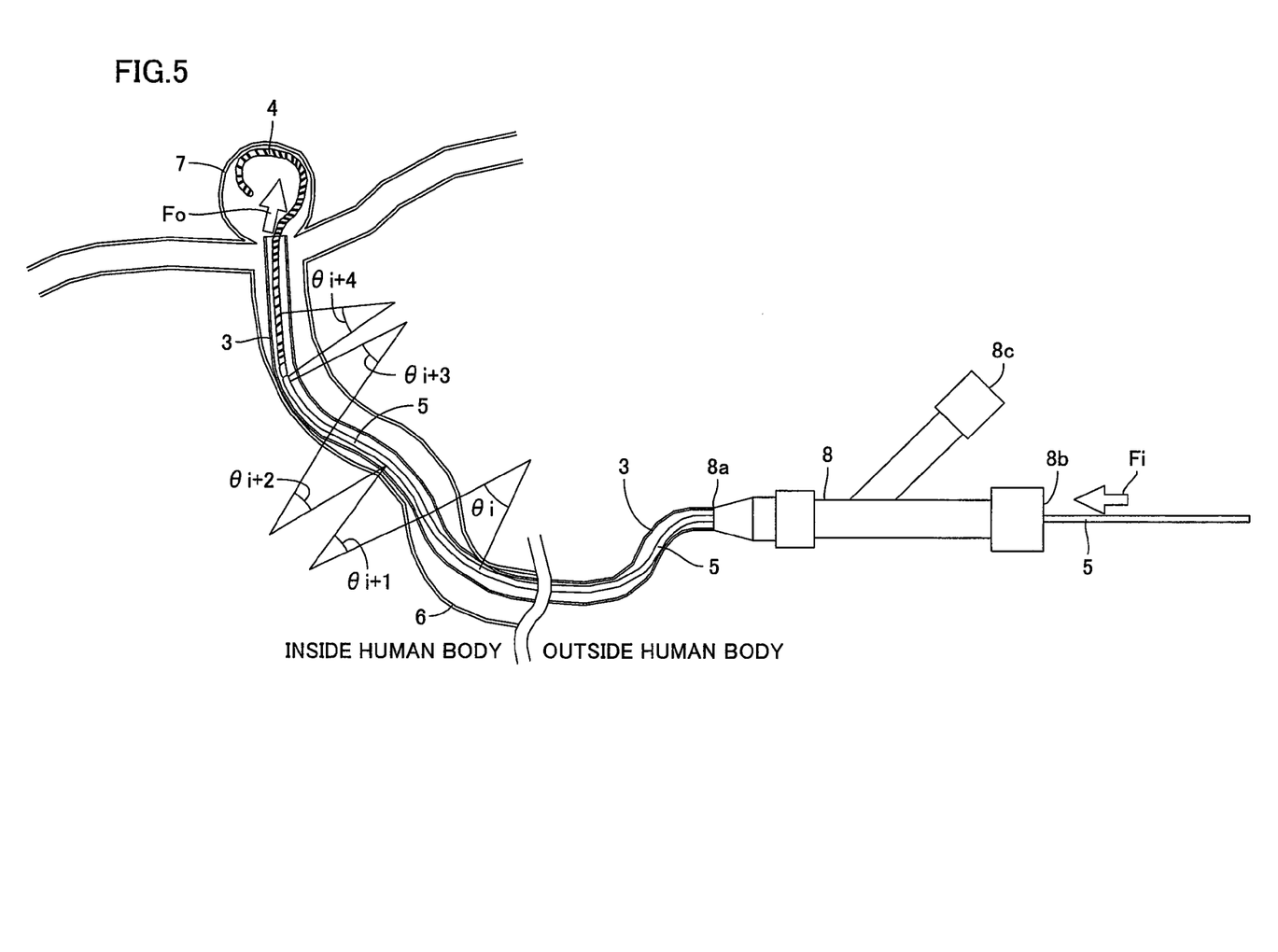
FIG. 5 is a diagram showing a load detection method according to Embodiment 2 of the present invention.

FIG. 5 is a diagram showing a load detection method according to Embodiment 2 of the present invention. Present Embodiment 2 is an application of the load detection method in Embodiment 1 to treatment for embolizing a cerebral aneurysm. In FIG. 5, a catheter 3 is employed as hollow tube 1, and an embolization coil 4 and a delivery wire 5 are employed as linear body 2 having flexibility. A base end of embolization coil 4 is coupled to a tip end of delivery wire 5. A cerebral aneurysm 7 has occurred in a part of a cerebral artery 6 of a patient. A tip end of catheter 3 is inserted in an artery of the patient from outside of his/her body and guided to a mouth of cerebral aneurysm 7 through cerebral artery 6. A base end of catheter 3 is connected to an outlet 8a of a Y-connector 8. After the tip end of catheter 3 is guided to the mouth of cerebral aneurysm 7 by using a guide wire (not shown), a tip end of embolization coil 4 is inserted through an inlet 8b of Y-connector 8. In succession to embolization coil 4, delivery wire 5 is inserted through inlet 8b of Y-connector 8 so that cerebral aneurysm 7 is filled with embolization coil 4 through catheter 3. Here, delivery wire 5 is inserted while load Fo applied to the tip end of embolization coil 4 is detected with the method shown in Embodiment 1. During a surgical operation, physiological saline is injected into catheter 3 through another inlet 8c of Y-connector 8. After embolization coil 4 is rested in cerebral aneurysm 7, delivery wire 5 is detached from embolization coil 4, catheter 3 and delivery wire 5 are pulled out of the body, and thus the surgical operation ends.

Such treatment for embolizing cerebral aneurysm 7 is given while a human body is subjected to fluoroscopy using X-ray equipment. As catheter 3 is made of resin, it is not displayed in a fluoroscopic image. On the other hand, embolization coil 4 and delivery wire 5 are made of metal, they are displayed in a fluoroscopic image. A fluoroscopic image is normally a two-dimensional image, however, in treatment for embolizing cerebral aneurysm 7, in order to observe a state of embolization coil 4 in cerebral aneurysm 7, the X-ray equipment is of a revolving type, so that a three-dimensional image can be created from a plurality of two-dimensional perspective images taken while the X-ray equipment revolves.

In treatment for embolizing cerebral aneurysm 7, cerebral aneurysm 7 of which blood vessel wall is thin and fragile should be filled with embolization coil 4 so as not to cause rupture of cerebral aneurysm 7 and hence force Fo applied to cerebral aneurysm 7 by embolization coil 4 is desirably measured. In present Embodiment 2, degrees of bending $\theta$ of embolization coil 4 and delivery wire 5 within catheter 3 are summed based on fluoroscopic images, load Fi in inserting delivery wire 5 is measured, and force Fo applied to cerebral aneurysm 7 by embolization coil 4 is estimated.

Figure 6:
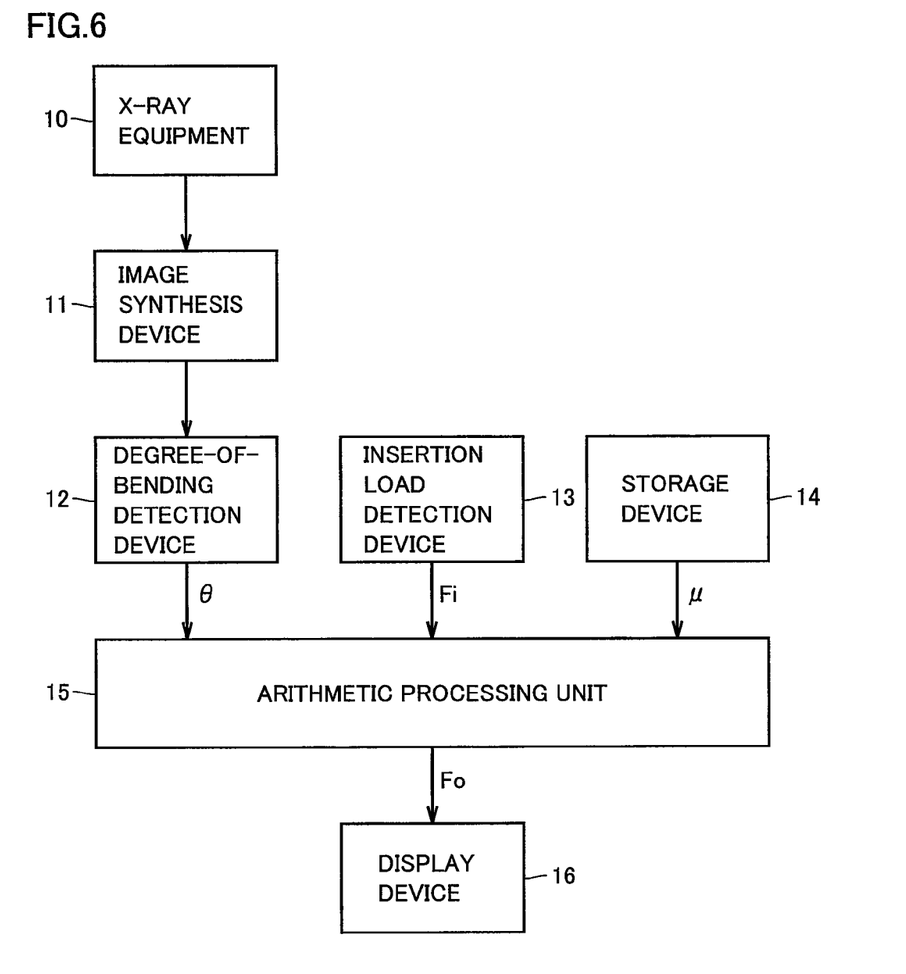
FIG. 6 is a block diagram showing a structure of a load detection device for performing the load detection method shown in FIG. 5.

FIG. 6 is a block diagram showing a structure of a load detection device for performing the load detection method in present Embodiment 2. In FIG. 6, this load detection device includes X-ray equipment 10, an image synthesis device 1, a degree-of-bending detection device 12, an insertion load detection device 13, a storage device 14, an arithmetic processing unit 15, and a display device 16.

X-ray equipment 10 takes a plurality of two-dimensional perspective images while revolving around a patient. Image synthesis device 1 creates a three-dimensional image from two-dimensional images taken by X-ray equipment 10. Degree-of-bending detection device 12 detects degree of bending $\theta$ of embolization coil 4 and delivery wire 5 based on the three-dimensional image created by image synthesis device 1. Insertion load detection device 13 detects load Fi in insertion of delivery wire 5. Storage device 14 stores coefficient of friction $\mu$ between embolization coil 4, delivery wire 5 and catheter 3 measured in advance.

Arithmetic processing unit 15 calculates load Fo at the tip end applied to cerebral aneurysm 7 by embolization coil 4, based on degree of bending $\theta$ of embolization coil 4 and delivery wire 5 detected by degree-of-bending detection device 12, load Fi in insertion of delivery wire 5 detected by insertion load detection device 13, and coefficient of friction $\mu$ stored in storage device 14. This calculation method is as described in Embodiment 1. Display device 16 displays load Fo at the tip end. A doctor gives embolizing treatment while viewing load Fo at the tip end displayed on display device 16.

[Embodiment 3]

Though a degree of bending of delivery wire 5 or the like during coil embolization is found in Embodiment 2, a degree of bending of delivery wire 5 or the like before treatment is found in present Embodiment 3. In treatment for embolizing cerebral aneurysm 7 with a coil, in order to check a size and presence of cerebral aneurysm 7 before treatment, an X-ray CT (computerized tomography system) or an MRI (nuclear magnetic resonance imaging system) is used to take a three-dimensional blood vessel image as shown in FIG. 7.

In treatment, catheter 3 is inserted from an artery at the base of a femoral region and sent from an aorta 20 through a carotid artery 21 (or a vertebral artery 22) and cerebral artery 6 to cerebral aneurysm 7. As catheter 3 is bent along the blood vessel, bending of embolization coil 4 and delivery wire 5 that pass therethrough is also substantially the same as bending of the blood vessel. Therefore, by using a degree of bending of a blood vessel path to cerebral aneurysm 7, force applied to cerebral aneurysm 7 by embolization coil 4 can be guessed as in Embodiment 2.

Figure 7:
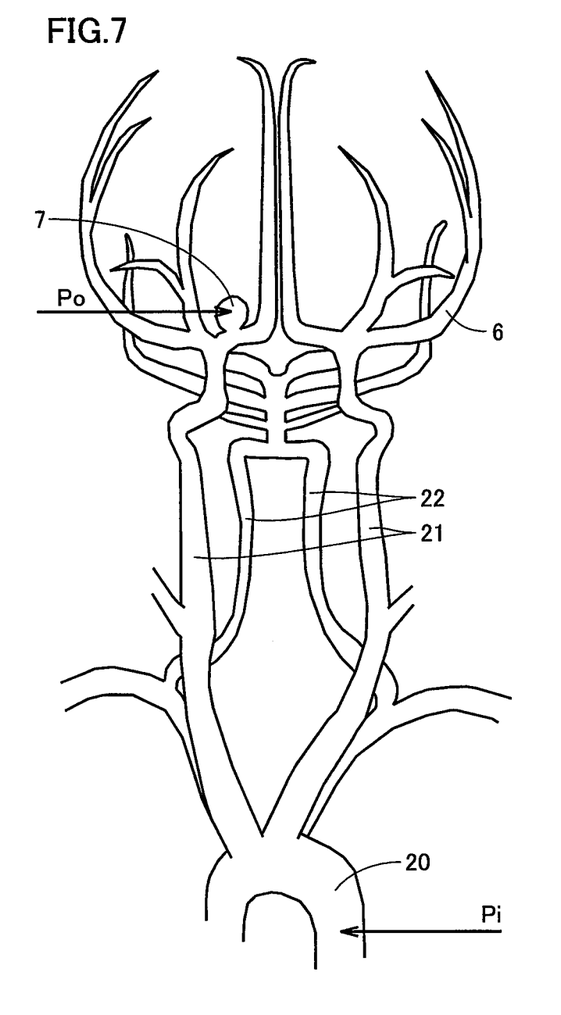
FIG. 7 is a diagram showing a load detection method according to Embodiment 3 of the present invention.
Figure 8:
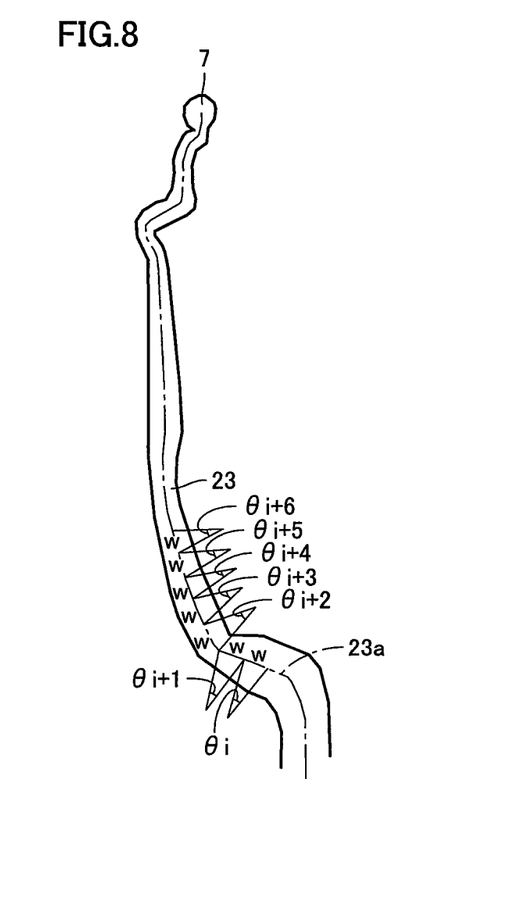
FIG. 8 is a diagram showing a method of finding load at the tip end based on a three-dimensional blood vessel image shown in FIG. 7.

Specifically, after the three-dimensional blood vessel image as shown in FIG. 7 is obtained, a doctor designates a position of cerebral aneurysm 7 (a catheter tip end position Po) and a position of a lowermost portion through which catheter 3 passes (for example, aorta 20) (a catheter insertion position Pi) as viewed in the image. A blood vessel from an artery at the base of a leg to aorta 20 is greater in diameter than cerebral artery 6 and substantially straight, and difference among patients is not great. Therefore, in estimating load Fo at the tip end, it suffices that friction in this region is set to either zero or a constant value. Then, as shown in FIG. 8, a blood vessel 23 between cerebral aneurysm 7 and aorta 20 selected by the doctor is extracted. Regarding a path of this blood vessel 23, by finding a centerline 23a of blood vessel 23, finding degrees of bending $\theta i$ of centerline 23a, for example, at prescribed intervals w, and summing $\theta i$ ($\Sigma \theta i$), force Fo applied to cerebral aneurysm 7 by embolization coil 4 can be estimated.

Though centerline 23a of blood vessel 23 is found after a path of blood vessel 23 is extracted in present Embodiment 3, a centerline of the entire blood vessel may be found in image processing in advance and then a path of a blood vessel through which catheter 3 passes may be found based on the path of the centerline.

[Embodiment 4]

Figure 9:
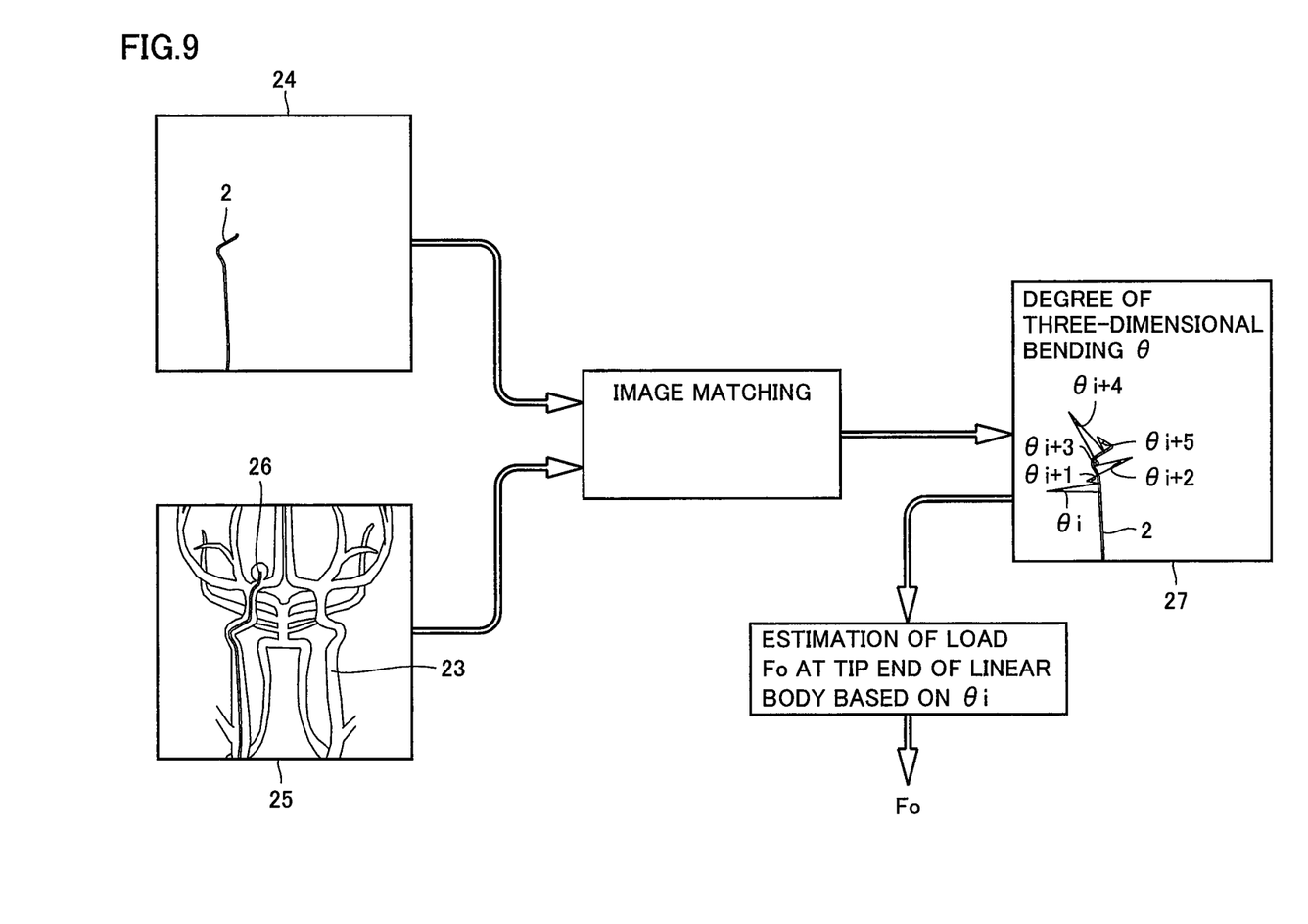
FIG. 9 is a diagram showing a load detection method according to Embodiment 4 of the present invention.

FIG. 9 is a block diagram showing a load detection method according to Embodiment 4 of the present invention. According to this load detection method, load Fo at the tip end is detected while linear body 2 is being inserted. In FIG. 9, linear body 2 is inserted in a human body while a doctor is observing a fluoroscopic two-dimensional image 24. In fluoroscopic two-dimensional image 24, a degree of three-dimensional bending of linear body 2 cannot be seen.

By combining fluoroscopic two-dimensional image 24 and a three-dimensional blood vessel image 25 taken prior to a surgical operation with each other, however, a degree of three-dimensional bending of linear body 2 can be estimated. Since linear body 2 has been inserted in blood vessel 23 and in addition a path 26 from an insertion port to a destination (cerebral aneurysm 7) has been known, a position of linear body 2 in three-dimensional blood vessel image 25 can be known by matching fluoroscopic two-dimensional image 24 and three-dimensional blood vessel image 25 with each other.

Thus, by using a degree of three-dimensional bending of blood vessel 23, degree of three-dimensional bending θ of linear body 2 can be known. Therefore, even during insertion of linear body 2 in a human body, load Fo at the tip end of linear body 2 can be estimated.

[Embodiment 5]

Figure 10:
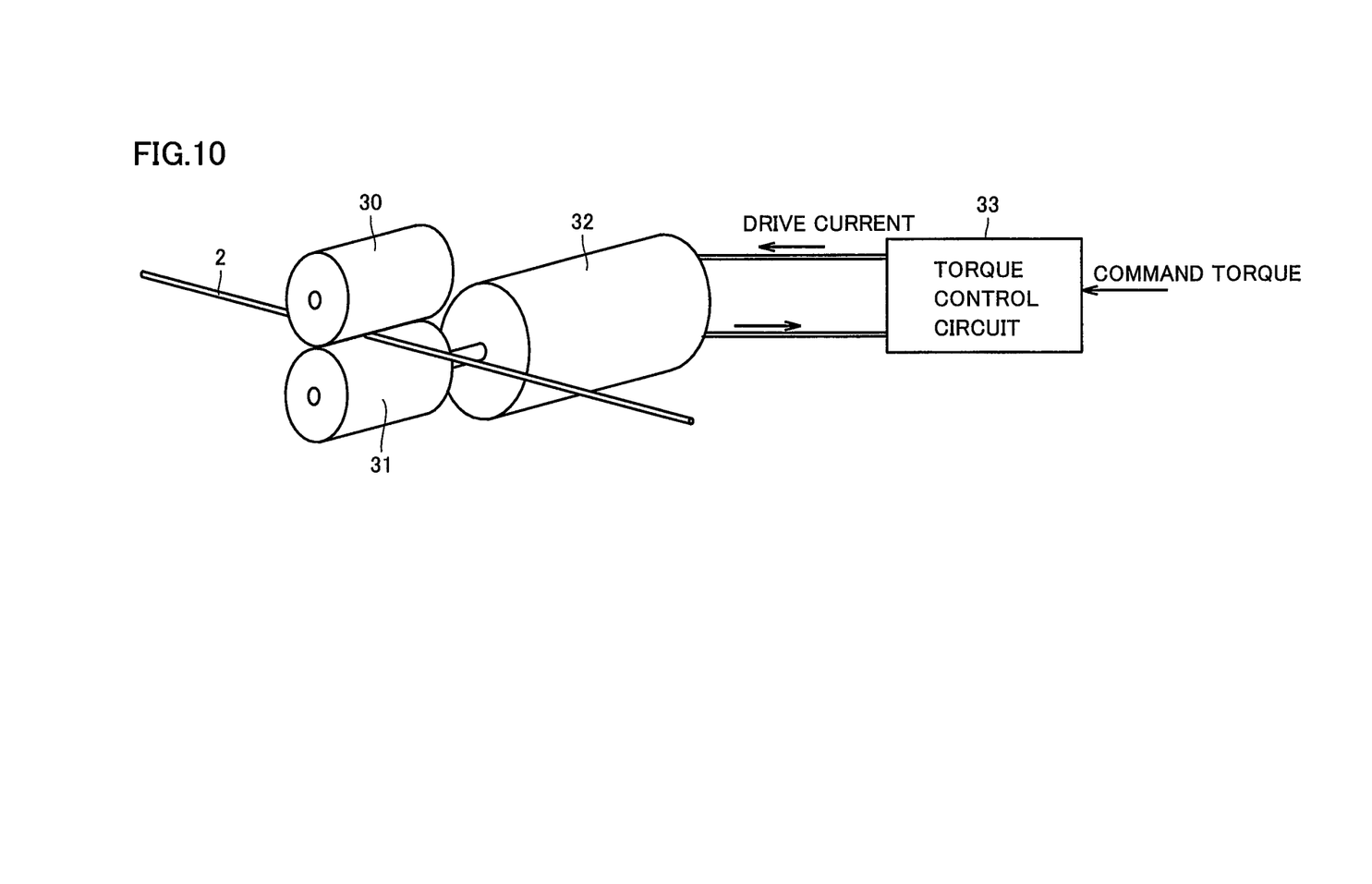
FIG. 10 is a diagram showing a structure of an insertion load detection device included in a load detection device according to Embodiment 5 of the present invention.

FIG. 10 is a block diagram showing a structure of an insertion load detection device included in a load detection device according to Embodiment 5 of the present invention. In FIG. 10, the insertion load detection device includes a pressing roller 30, a drive roller 31, a motor 32, and a torque control circuit 33. An outer circumferential portion of each of rollers 30 and 31 is formed of such an elastic body as rubber. Pressing roller 30 is rotatably supported and pressed toward drive roller 31 with a prescribed pressure. Therefore, pressing roller 30 is driven together with drive roller 31.

Linear body 2 such as delivery wire 5 is inserted in hollow tube 1 as it passes between rollers 30 and 31. Drive roller 31 is rotatably driven by motor 32. Torque control circuit 33 supplies a drive current to motor 32 in accordance with a torque command value and outputs a signal indicating a drive current value to arithmetic processing unit 15 in FIG. 6, instead of insertion load Fi.

As the drive current is supplied from torque control circuit 33 to motor 32, motor 32 rotatably drives rollers 30 and 31 at a low speed so that linear body 2 is inserted in hollow tube 1. Arithmetic processing unit 15 in FIG. 6 calculates load Fi in insertion of linear body 2 based on a signal from torque control circuit 33 and finds load Fo at the tip end by using that insertion load Fi.

According to present Embodiment 5, load Fi in insertion of linear body 2 can readily be detected.

[Embodiment 6]

Figure 11:
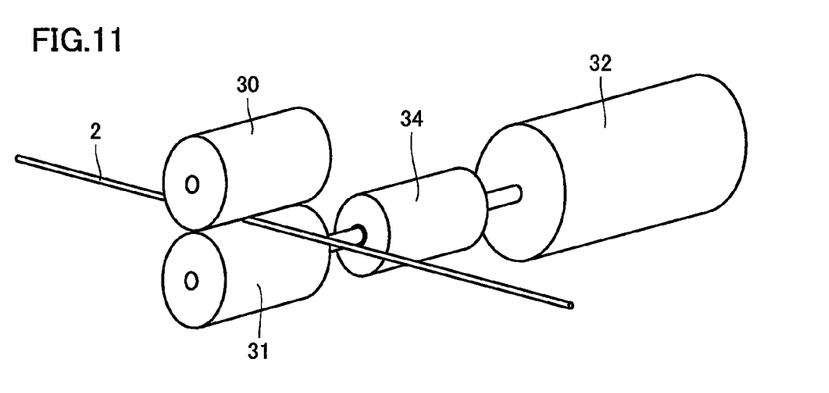
FIG. 11 is a diagram showing a structure of an insertion load detection device included in a load detection device according to Embodiment 6 of the present invention.

FIG. 11 is a diagram showing a structure of an insertion load detection device included in a load detection device according to Embodiment 6 of the present invention, and it is compared with FIG. 10. The insertion load detection device in FIG. 11 is different from the insertion load detection device in Embodiment 5 in that a torque sensor 34 is provided between a rotation shaft of motor 32 and a rotation shaft of drive roller 31. A strain gauge or a magnetostrictive torque sensor is employed as torque sensor 34. Torque sensor 34 detects strain of a shaft coupling the rotation shaft of motor 32 and the rotation shaft of drive roller 31 to each other and outputs a signal indicating the detected value to arithmetic processing unit 15 in FIG. 6, instead of insertion load Fi.

When the drive current is supplied to motor 32, motor 32 rotatably drives rollers 30 and 31 at a low speed so that linear body 2 is inserted in hollow tube 1. Arithmetic processing unit 15 in FIG. 6 calculates load Fi in insertion of linear body 2 based on a signal from torque sensor 34 and finds load Fo at the tip end by using that insertion load Fi.

According to present Embodiment 6 as well, load Fi in insertion of linear body 2 can readily be detected.

[Embodiment 7]

Figure 12:
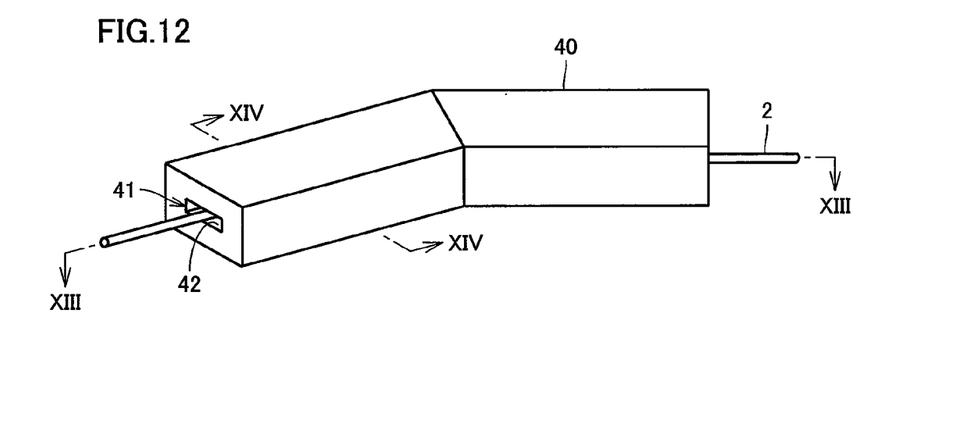
FIG. 12 is a diagram showing a main body portion of an insertion load detection device included in a load detection device according to Embodiment 7 of the present invention.
Figure 13:
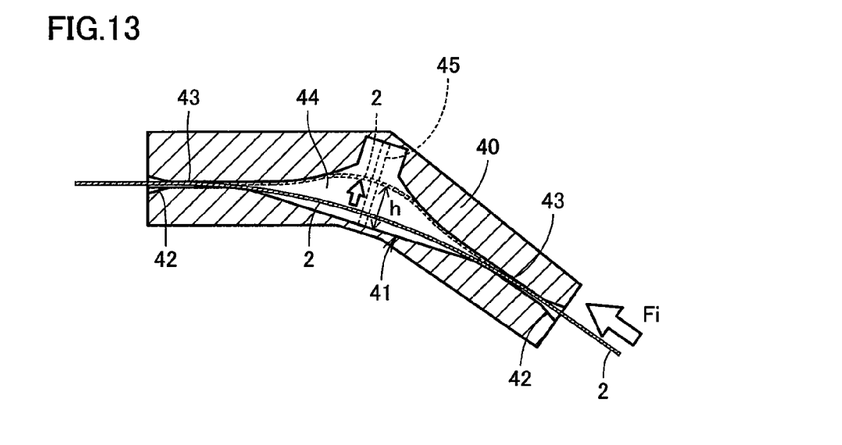
FIG. 13 is a cross-sectional view along the line XIII-XIII in FIG. 12.
Figure 14:
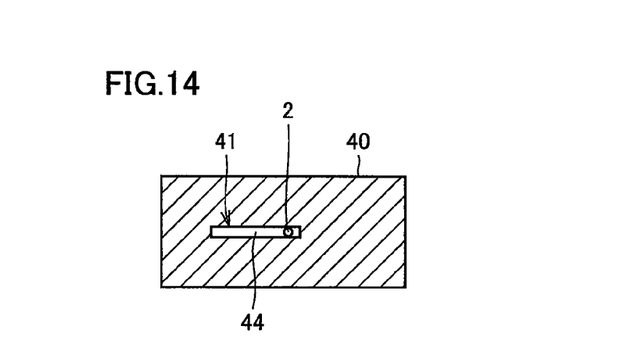
FIG. 14 is a cross-sectional view along the line XIV-XIV in FIG. 12.

FIG. 12 is a diagram showing appearance of a main portion of an insertion load detection device according to Embodiment 7 of the present invention, FIG. 13 is a cross-sectional view along the line XIII-XIII in FIG. 12, and FIG. 14 is a cross-sectional view along the line XIV-XIV in FIG. 12. In FIGS. 12 to 14, the insertion load detection device includes a main body portion 40, and a through hole 41 through which linear body 2 passes is formed in main body portion 40. One end of linear body 2 is operated with a hand of an operator and the other end of linear body 2 is inserted in hollow tube 1 inserted in a vessel of a human body.

A tapered input and output port 42 is formed at each of opening portions at respective opposing ends of through hole 41, for facilitating insertion and extraction of linear body 2. In a restraint portion 43 in the rear of input and output port 42, a diameter of through hole 41 is slightly greater than a diameter of linear body 2, and it is set, for example, to 105% to 120% of the diameter of linear body 2. Therefore, in restraint portion 43, linear body 2 cannot move in a direction other than a direction of longitudinal axis.

When insertion load Fi in the direction of longitudinal axis is applied to linear body 2, main body portion 40 defines a direction of curve of linear body 2 within through hole 41. Namely, through hole 41 is bent between two restraint portions 43 and linear body 2 passes through through hole 41 while bending along one wall. In addition, through hole 41 forms a space 44 between two restraint portions 43, that extends toward a wall along which linear body 2 does not extend. Therefore, in space 44, an operation of linear body 2 in a direction in parallel to the sheet surface is not restricted by through hole 41.

On the other hand, in input and output port 42 and space 44, a height of through hole 41 in a direction perpendicular to the sheet surface is slightly greater than a diameter of linear body 2, and it is set, for example, to 105% to 120% of the diameter of linear body 2. Therefore, an operation of linear body 2 in the direction perpendicular to the sheet surface is restricted by through hole 41. Namely, in input and output port 42 and space 44, a cross-sectional shape of through hole 41 in a cross-section perpendicular to the direction of longitudinal axis of linear body 2 is rectangular as shown in FIG. 14. The direction of curve of linear body 2 within through hole 41 is thus defined and a position where linear body 2 curves at the time when insertion load Fi in the direction of longitudinal axis is applied to linear body 2 is determined.

As shown in FIG. 13, when insertion load Fi in the direction of longitudinal axis is applied to linear body 2, linear body 2 curves in a prescribed direction in space 44 inside through hole 41, that is, toward the wall along which linear body 2 does not extend in space 44. As linear body 2 curves, a height h of peak of curve, that is, a distance from a wall surface along which linear body 2 extends to linear body 2 increases. In main body portion 40, an optical line sensor 45 for detecting height h of the peak of curve is embedded.

Figure 15:
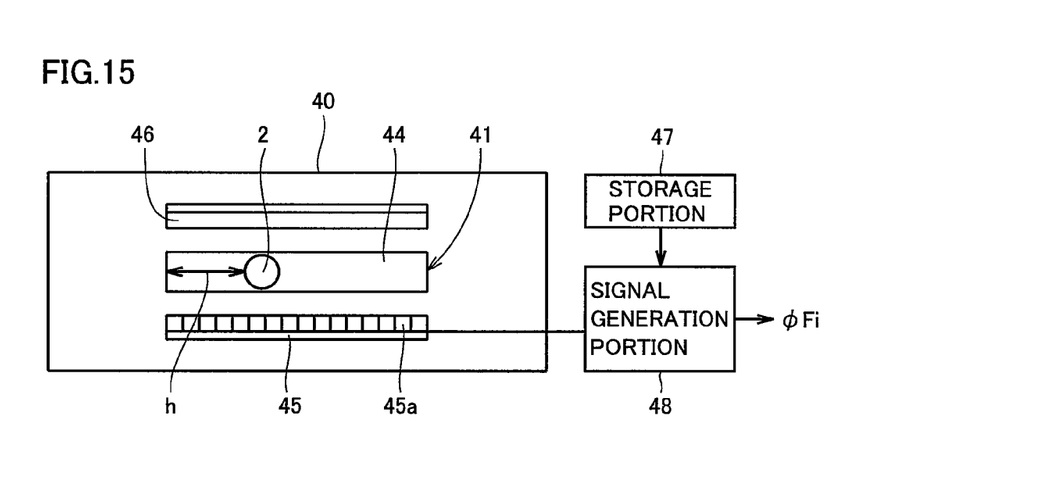
FIG. 15 is a diagram showing an overall structure of the insertion load detection device shown in FIG. 12.

As shown in FIG. 15, line sensor 45 is an array sensor having a plurality of light-receiving elements 45a aligned in a direction of height h of curve of linear body 2. A light source device 46 is embedded in main body portion 40 on the side opposite to line sensor 45, with space 44 in through hole 41 being interposed. Light source device 46 emits illumination light toward line sensor 45 through space 44.

The illumination light emitted from light source device 46 is incident on line sensor 45 where linear body 2 is absent, however, it is cut off by linear body 2 where linear body 2 is present and is not incident on line sensor 45. In other words, a shadow of linear body 2 is cast on line sensor 45. A large photocurrent is generated in light-receiving element 45a that receives the illumination light, but a photocurrent is hardly generated in light-receiving element 45a located in the shadow of linear body 2. Therefore, by detecting a photocurrent of each light-receiving element 45a, a position of linear body 2 within space 44, that is, height h of curve of linear body 2, can be found.

The insertion load detection device further includes a storage portion 47 and a signal generation portion 48. Storage portion 47 stores a table showing correlation between height h of curve of linear body 2 and insertion load Fi. Signal generation portion 48 finds height h of curve of linear body 2 by detecting a photocurrent of each light-receiving element 45a, finds insertion load Fi corresponding to that height h by referring to the table in storage portion 47, and outputs a signal ΦFi indicating that insertion load Fi to arithmetic processing unit 15 in FIG. 6. Arithmetic processing unit 15 in FIG. 6 finds load Fo at the tip end based on signal ΦFi from signal generation portion 48.

According to present Embodiment 7 as well, load Fi in insertion of linear body 2 can readily be detected.

[Embodiment 8]

Figure 16:
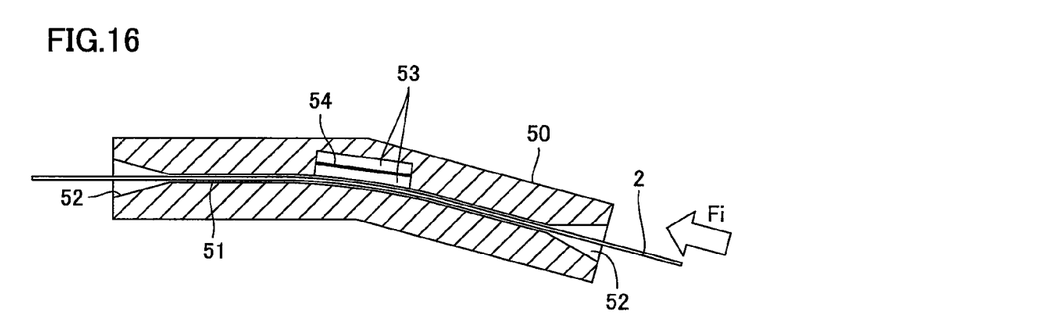
FIG. 16 is a diagram showing a structure of an insertion load detection device included in a load detection device according to Embodiment 8 of the present invention.

FIG. 16 is a cross-sectional view showing a main portion of an insertion load detection device according to Embodiment 8 of the present invention, and it is compared with FIG. 13. In FIG. 16, the insertion load detection device includes a main body portion 50, and a through hole 51 through which linear body 2 passes is formed in main body portion 50. One end of linear body 2 is operated with a hand of an operator and the other end of linear body 2 is inserted in hollow tube 1 inserted in a vessel of a human body.

A tapered input and output port 52 is formed at each of opening portions at respective opposing ends of through hole 51, for facilitating insertion and extraction of linear body 2. A diameter of through hole 51 is slightly greater than a diameter of linear body 2, and it is set, for example, to 105% to 120% of the diameter of linear body 2. Through hole 51 is bent in an arc shape in a central portion in a direction of length, and linear body 2 passes through through hole 51 while it is bent. An elastic member 53 is embedded on an outer side (an upper side in FIG. 16) of an arc-shaped portion in the central portion of through hole 51 and a strain sensor 54 is provided within elastic member 53.

Linear body 2 is inserted in through hole 51 as it is bent. Therefore, when insertion load Fi is applied to linear body 2, a central portion curved in an arc-shape tends to further bend and a pressure is applied to strain sensor 54 through elastic member 53. Therefore, load Fi in insertion of linear body 2 can be detected based on an output signal from strain sensor 54. Arithmetic processing unit 15 in FIG. 6 finds insertion load Fi from strain sensor 54 and finds load Fo at the tip end based on that insertion load Fi.

According to present Embodiment 8 as well, load Fi in insertion of linear body 2 can readily be detected.

[Embodiment 9]

Figure 17:
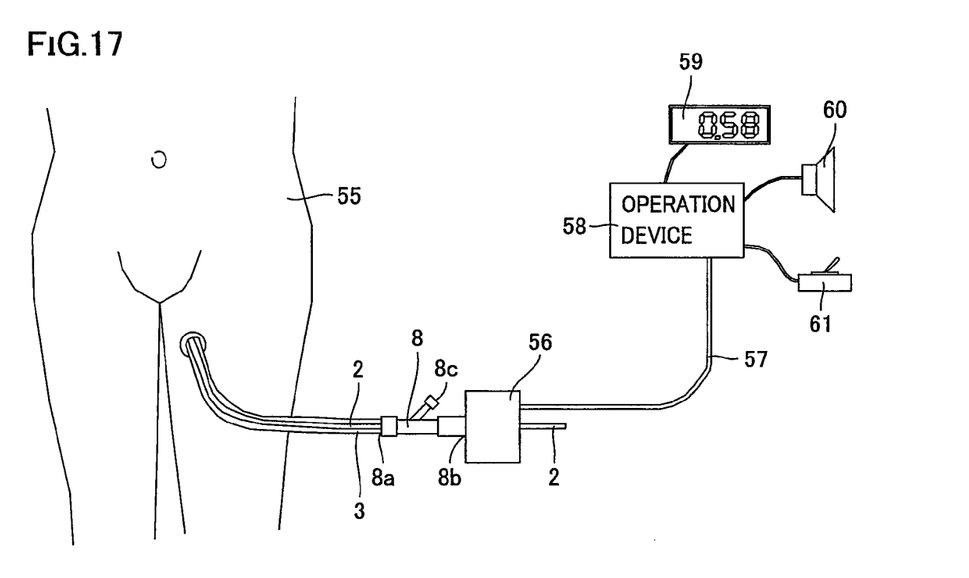
FIG. 17 is a diagram showing a structure of medical equipment according to Embodiment 9 of the present invention.

FIG. 17 is a diagram showing a structure of medical equipment according to Embodiment 9 of the present invention. In FIG. 17, the tip end of catheter 3 is inserted in an artery at the base of the leg of a human body 55 and guided, for example, to a mouth of cerebral aneurysm 7. The base end of catheter 3 is connected to outlet 8a of Y-connector 8. An insertion load detection device 56 is attached to one inlet 8b of Y-connector 8 and physiological saline is injected into catheter 3 through another inlet 8c.

For example, the device shown in Embodiments 7 and 8 is used as insertion load detection device 56. Insertion load detection device 56 and Y-connector 8 may integrally be formed. Linear body 2 is inserted in catheter 3 through insertion load detection device 56 and Y-connector 8. A degree of bending of linear body 2 is found, for example, with the method shown in Embodiments 3 and 4.

An output signal from insertion load detection device 56 is provided to an operation device 58 through a cable 57. A display 59, a speaker 60 and a switch 61 are connected to operation device 58. Operation device 58 finds load Fo at the tip end of linear body 2 based on the output signal from insertion load detection device 56, a degree of bending of linear body 2, and the like.

Display 59 provides visual display of load Fo at the tip end or insertion load Fi by using numerics. Speaker 60 gives aural notification of load Fo at the tip end or insertion load Fi by using tone, volume or the like. Switch 61 switches between display 59 and speaker 60, for providing display or giving notification of any of load Fo at the tip end and insertion load Fi. A doctor can know load Fo at the tip end or insertion load Fi by viewing display on display 59 or listening to sound from speaker 60, and operates linear body 2 based thereon.

[Embodiment 10]

Figure 18:
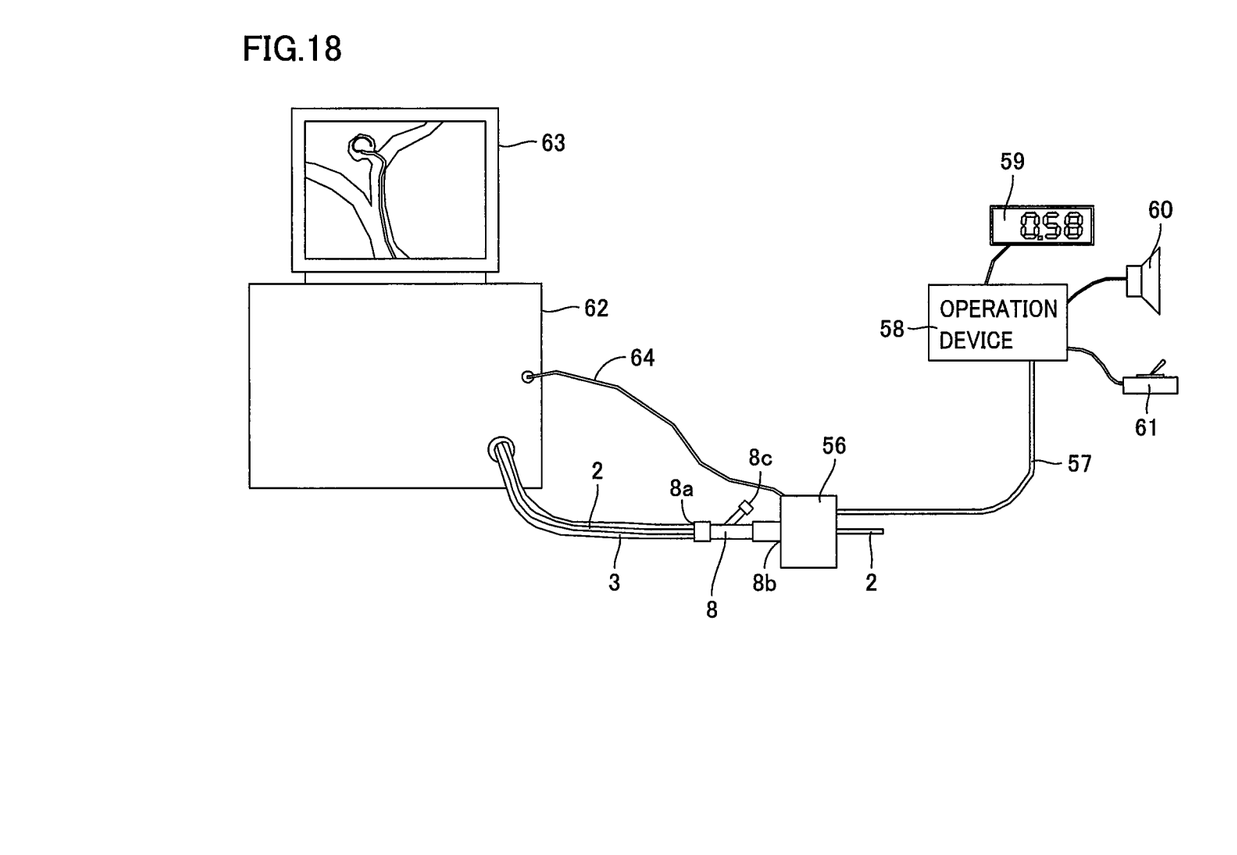
FIG. 18 is a diagram showing a structure of medical training equipment according to Embodiment 10 of the present invention.

FIG. 18 is a block diagram showing a structure of medical training equipment According to Embodiment 10 of the present invention, and it is compared with FIG. 17. In FIG. 18, in this medical training equipment, a simulator 62 is used instead of human body 55. Simulator 62 causes a monitor 63 to display a simulated perspective image equivalent to a fluoroscopic image of a vessel in a human body in which linear body 2 is inserted. Linear body 2 is, for example, embolization coil 4 and delivery wire 5 inserted in catheter 3 of which tip end is disposed at the mouth of cerebral aneurysm 7. Simulator 62 varies insertion resistance of inserted linear body 2. Resistance force at the time of operation, that is, load Fi in insertion of linear body 2, is transmitted also to simulator 62 through a cable 64. Simulator 62 varies insertion resistance of linear body 2 in accordance with insertion load Fi.

An operator in training operates linear body 2 while viewing a simulated perspective image displayed on monitor 63 and insertion load Fi or load Fo at the tip end displayed on display 59 and further listening to sound from speaker 60 indicating insertion load Fi or load Fo at the tip end. The simulated perspective image, insertion load Fi and load Fo at the tip end during operation are recorded in a video image recording medium within a video image recording apparatus (not shown). The record is utilized for training or evaluation of an operator. In addition, the video image recording medium records a simulated perspective image, insertion load Fi, load Fo at the tip end, and a commentary by a person of skill at the time when he/she operates linear body 2 in simulator 62. A less experienced operator can reproduce the operation records of the person of skill and learn his/her manipulation.

According to present Embodiment 10, manipulation of a skilled operator can be quantified and transferred to a less experienced operator, so that manipulation of the less experienced operator can quickly be improved.

It should be understood that the embodiments disclosed herein are illustrative and non-restrictive in every respect. The scope of the present invention is defined by the terms of the claims, rather than the description above, and is intended to include any modifications within the scope and meaning equivalent to the terms of the claims.

The invention claimed is:

1. A load detection device for detecting load applied to a tip end of a linear body having flexibility when said linear body is inserted in a hollow tube inserted in a bending vessel, comprising:
    a degree of bending detection device configured to detect a degree of bending of said vessel, said hollow tube, or said linear body;
    an insertion load detection device configured to detect load in insertion of said linear body in an inlet of said hollow tube; and
    a processing unit communicatively coupled to the degree of bending detection device and to the insertion load detection device and configured to find the load applied to the tip end of said linear body based on a result of detection by the degree of bending detection device and the insertion load detection device, and based on a coefficient of friction between the linear body and the hollow tube,
wherein said processing unit is further configured to correct said coefficient of friction based on variation in flexural rigidity depending on a position in said linear body where the flexural rigidity of said linear body varies depending on the position in said linear body.

2. The load detection device according to claim 1, wherein said degree of bending detection device is further configured to detect the degree of bending of said vessel, said hollow tube, or said linear body based on an image of said vessel, said hollow tube, or said linear body.

3. The load detection device according to claim 1, wherein said coefficient of friction is measured in advance.

4. The load detection device according to claim 1, wherein
said vessel is a blood vessel,
said hollow tube is a catheter, and
said linear body is a treatment wire to be inserted in said catheter.

5. The load detection device according to claim 4, wherein said treatment wire includes a delivery wire and an embolization coil provided at a tip end portion of the delivery wire, for filling a cerebral aneurysm.

6. The load detection device according to claim 5, wherein
said degree of bending detection device is further configured to detect a degree of bending of said treatment wire when a tip end of said embolization coil enters the cerebral aneurysm, and
said processing unit is further configured to find load applied to said cerebral aneurysm by said embolization coil.

7. The load detection device according to claim 4, wherein said degree of bending detection device is further configured to detect a degree of bending of said blood vessel based on a three-dimensional image of said blood vessel.

8. The load detection device according to claim 4, wherein said degree of bending detection device is further configured to detect a degree of bending of said treatment wire based on a two-dimensional image of said treatment wire taken by using X-rays during a surgical operation and a three-dimensional image of the blood vessel taken in advance, as superimposed on each other.

9. The load detection device according to claim 1, further comprising a drive unit coupled to the insertion load detection device and configured to insert said linear body in the inlet of said hollow tube,
wherein said insertion load detection device is further configured to detect the load in insertion of said linear body based on drive force of said drive unit.

10. The load detection device according to claim 1, further comprising:
a drive roller configured to insert said linear body in the inlet of said hollow tube;
a pressing roller rotatably supported and pressed by said drive roller with said linear body being interposed; and
a motor coupled to the driver roller and configured to rotatably drive said drive roller, wherein
said insertion load detection device is further configured to detect strain of a rotation shaft of said motor and detects the load in insertion of said linear body based on a result of that detection.

11. The load detection device according to claim 1, wherein said insertion load detection device includes:
a main body portion having a through hole through which said linear body passes and an internal space provided at an intermediate point of said through hole and formed such that said linear body can curve in a prescribed direction when compressive force is applied to said linear body, and
a curve sensor coupled to the main body portion and configured to detect a degree of curve of said linear body in said internal space, and
wherein said insertion load detection device is further configured to detect the load in insertion of said linear body based on said degree of curve detected by said curve sensor.

12. The load detection device according to claim 1, wherein said insertion load detection device includes:
a main body portion having a through hole through which said linear body passes and formed in a bent manner such that said linear body applies a pressure in a prescribed direction when compressive force is applied to said linear body, and
a pressure sensor provided at an intermediate point of said through hole, for detecting a pressure applied by said linear body in said prescribed direction, and
wherein said insertion load detection device is further configured to detect the load in insertion of said linear body based on a result of detection by said pressure sensor.

13. The load detection device according to claim 1, further comprising a display monitor configured to visually display at least one load of the load in insertion of said linear body detected by said insertion load detection device and the load applied to the tip end of said linear body found by said processing unit.

14. The load detection device according to claim 1, further comprising a speaker configured to generate sound indicating at least one load of the load in insertion of said linear body detected by said insertion load detection device and the load applied to the tip end of said linear body found by said processing unit.

15. The load detection device according to claim 1, further comprising a recording unit for recording in a video image recording medium together with a fluoroscopic image of a tip end portion of said linear body, at least one load of the load in insertion of said linear body detected by said insertion load detection device and the load applied to the tip end of said linear body found by said processing unit.

16. The load detection device according to any of claims 1-2 and 3-15, incorporated in a medical training apparatus.

17. A method comprising the steps of:
detecting, in a load detection device for detecting a load applied to a tip end of a linear body having flexibility when said linear body is inserted in a hollow tube inserted in a bending vessel, a degree of bending of said vessel, said hollow tube, or said linear body and load in insertion of said linear body in an inlet of said hollow tube; and
finding, by the load detection device, the load applied to the tip end of said linear body based on a result of that detection,
wherein the step of finding the load applied includes a calculation based on a coefficient of friction between the linear body and the hollow tube, and
wherein the step of finding the load applied includes correcting the coefficient of friction based on variation in flexural rigidity depending on a position in said linear body where the flexural rigidity of said linear body varies depending on the position in said linear body.

* * * * *